(12) United States Patent
Martin et al.

(10) Patent No.: US 11,011,254 B2
(45) Date of Patent: May 18, 2021

(54) CHEMICAL FORMULATION-AWARE COGNITIVE SEARCH AND ANALYTICS

(71) Applicant: INTERNATIONAL BUSINESS MACHINES CORPORATION, Armonk, NY (US)

(72) Inventors: Richard L. Martin, Jamaica Plain, MA (US); Katherine Shen, Corona, CA (US)

(73) Assignee: International Business Machines Corporation, Armonk, NY (US)

(*) Notice: Subject to any disclaimer, the term of this patent is extended or adjusted under 35 U.S.C. 154(b) by 182 days.

(21) Appl. No.: 16/049,913

(22) Filed: Jul. 31, 2018

(65) Prior Publication Data

US 2020/0042671 A1 Feb. 6, 2020

(51) Int. Cl.

| | |
|---|---|
| G06F 7/00 | (2006.01) |
| G06F 16/00 | (2019.01) |
| G16C 20/90 | (2019.01) |
| G06F 16/25 | (2019.01) |
| G06F 16/31 | (2019.01) |
| G06F 16/33 | (2019.01) |
| G16C 20/40 | (2019.01) |

(52) U.S. Cl.
CPC .......... G16C 20/90 (2019.02); G06F 16/258 (2019.01); G06F 16/316 (2019.01); G06F 16/3331 (2019.01); G16C 20/40 (2019.02)

(58) Field of Classification Search
None
See application file for complete search history.

(56) References Cited

U.S. PATENT DOCUMENTS

| | | | | |
|---|---|---|---|---|
| 8,865,757 | B1* | 10/2014 | Tabuteau | A61K 31/675 514/399 |
| 2005/0010603 | A1* | 1/2005 | Berks | G06F 40/106 |
| 2005/0203898 | A1 | 9/2005 | Boyer et al. | |
| 2007/0016612 | A1* | 1/2007 | James | G16C 20/40 |

(Continued)

OTHER PUBLICATIONS

IBM, "Getting Started," IBM Watson for Drug Discovery, Nov. 2017, 1 Page, Version 2.92, Grace Period Disclosure.

(Continued)

*Primary Examiner* — Tuan A Pham
(74) *Attorney, Agent, or Firm* — Dmitry Paskalov

(57) ABSTRACT

A method, computer system, and a computer program product for identifying and storing at least one representation to at least one chemical compound is provided. The present invention may include identifying a chemical compound associated with a source data. The present invention may also include assigning a structure representation to the identified chemical compound associated with the source data. The present invention may further include computing an unformulated representation based on the assigned structure representation. The present invention may then include indexing the computed unformulated representation and the assigned structure representation. The present invention may further include storing the indexed unformulated representation and the indexed structure representation separately as single records in a database.

19 Claims, 5 Drawing Sheets

(56) References Cited

U.S. PATENT DOCUMENTS

| | | | | |
|---|---|---|---|---|
| 2008/0004810 A1* | 1/2008 | Boyer | ................... | G16C 20/40 |
| | | | | 702/19 |
| 2011/0066632 A1* | 3/2011 | Robson | ................... | G06F 16/40 |
| | | | | 707/769 |
| 2012/0084299 A1* | 4/2012 | Cai | ....................... | G16C 20/40 |
| | | | | 707/748 |
| 2015/0065420 A1* | 3/2015 | Soliman | ............... | A61K 47/551 |
| | | | | 514/4.9 |
| 2016/0193214 A1* | 7/2016 | Amaro | ............... | A61K 31/4184 |
| | | | | 514/230.5 |
| 2017/0081536 A1* | 3/2017 | Brust | ................... | C09D 125/18 |

OTHER PUBLICATIONS

IBM, "Release Information," IBM Watson for Drug Discovery, Nov. 2017, p. 1-17, Version 2.92, Grace Period Disclosure.

Kiener, "Molecule Database Framework: A Framework for Creating Database Applications with Chemical Structure Search Capability," Journal of Cheminformatics, 2013, p. 1-13, vol. 5, Issue 48.

Mell et al., "The NIST Definition of Cloud Computing," National Institute of Standards and Technology, Sep. 2011, p. 1-3, Special Publication 800-145.

Pubchem, "About PubChem," PubChem Docs, p. 1-2, National Institutes of Health (NIH), https://pubchemdocs.ncbi.nlm.nih.gov/about, Accessed on Jul. 12, 2018.

Rhodes et al., "Mining Patents Using Molecular Similarity Search," Pacific Symposium on Biocomputing, 2007, 12 Pages.

Sun et al., "Identifying, Indexing, and Ranking Chemical Formulae and Chemical Names in Digital Documents," ACM Transactions on Information Systems, Apr. 2011, p. 1-38, vol. 29, No. 2, Article 12.

Yan et al., "Chemical Name Extraction Based on Automatic Training Data Generation and Rich Feature Set," IEEE/ACM Transactions on Computational Biology and Bioinformatics, Sep./Oct. 2013, p. 1218-1233, vol. 10, No. 5, Published by the IEEE CS, CI, and EMB Societies & the ACM.

* cited by examiner

CHEMICAL FORMULATION-AWARE COGNITIVE SEARCH AND ANALYTICS

STATEMENT REGARDING PRIOR DISCLOSURES BY THE INVENTOR OR A JOINT INVENTOR

Aspects of the present invention have been disclosed by the Applicant, who obtained the subject matter disclosed directly from the inventors, in the product IBM Watson for Drug Discovery, Version 2.92, made available to the public on Nov. 2, 2017. The following disclosure is submitted under 35 U.S.C. § 102(b)(1)(A).

BACKGROUND

The present invention relates generally to the field of computing, and more particularly to drug research.

The creation of new chemical products is fundamentally important to multiple industries, including pharmaceuticals, agrochemicals, biotechnology, and other related areas. Due to the practically unlimited space of possible chemicals, there is a significant market for chemical information services and other products through which chemicals can be searched, browsed, compared, purchased, analyzed, predicted upon and so on. However, search and analytics of chemical products is particularly complex due in large part to the importance of chemical formulations.

Broadly, a chemical formulation is the way a chemical product is prepared and provided for use. For instance, while the active ingredient of a medication may be the compound known as montelukast, the actual formulation of this product for use as an injection may comprise the active ingredient in a sodium solution, namely montelukast sodium. Depending on the route of administration (e.g., injection, oral), dosage, stability and many other factors, there may be many formulations of a single active ingredient on the market, or in various stages of research or clinical trials.

SUMMARY

Embodiments of the present invention disclose a method, computer system, and a computer program product for identifying and storing at least one representation to at least one chemical compound. The present invention may then include identifying at least one chemical compound associated with at least one set of source data. The present invention may also include assigning at least one structure representation to the identified at least one chemical compound associated with the at least one set of source data. The present invention may further include computing one or more unformulated representation(s) based on the assigned at least one structure representation. The present invention may then include indexing the computed one or more unformulated representations and the assigned at least one structure representation. The present invention may further include storing the indexed one or more unformulated representations and the indexed at least one structure representation separately as a single record in a cognitive search and analytics database.

BRIEF DESCRIPTION OF THE SEVERAL VIEWS OF THE DRAWINGS

These and other objects, features and advantages of the present invention will become apparent from the following detailed description of illustrative embodiments thereof, which is to be read in connection with the accompanying drawings. The various features of the drawings are not to scale as the illustrations are for clarity in facilitating one skilled in the art in understanding the invention in conjunction with the detailed description. In the drawings.

DETAILED DESCRIPTION

Figure 1:
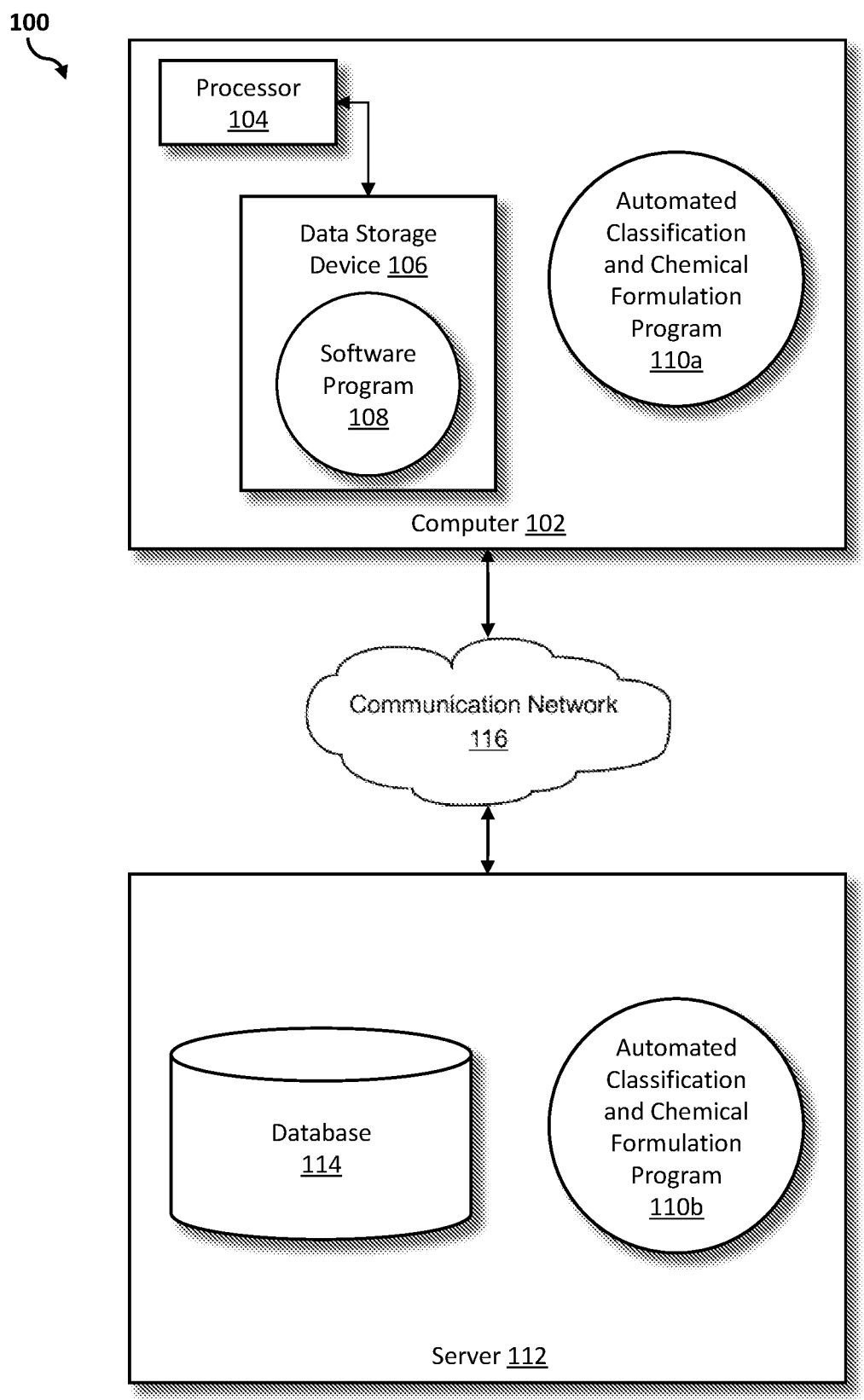
FIG. 1 illustrates a networked computer environment according to at least one embodiment.

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. Rather, these exemplary embodiments are provided so that this disclosure will be thorough and complete and will fully convey the scope of this invention to those skilled in the art. In the description, details of well-known features and techniques may be omitted to avoid unnecessarily obscuring the presented embodiments.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language, Python programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The following described exemplary embodiments provide a system, method and program product for identifying and storing at least one representation for at least one chemical compound. As such, the present embodiment has the capacity to improve the technical field of drug research by utilizing the structural information of a chemical compound to assign an unformulated, active ingredient form. More specifically, the automated classification and chemical formulation program may perform an automated generation of an unformulated representation (i.e., simplified structure representation) for compounds, and index and store these unformulated representations as a single record, with a direct linkage to the structure representation.

As previously described, the creation of new chemical products is fundamentally important to multiple industries, including pharmaceuticals, agrochemicals, biotechnology, and other related areas. Due to the practically unlimited space of possible chemicals, there is a significant market for chemical information services and other products through which chemicals can be searched, browsed, compared, purchased, analyzed, predicted upon and so on. However, search and analytics of chemical products is particularly complex due in large part to the importance of chemical formulations.

Broadly, a chemical formulation (i.e., representation) is the way a chemical product is prepared and provided for use. For instance, while the active ingredient of a medication may be the compound known as montelukast, the actual formulation of this product for use as a tablet may comprise the active ingredient with a sodium salt, namely montelukast sodium. Depending on the route of administration (e.g., injection, oral), dosage, stability and many other factors, there may be many formulations of a single active ingredient on the market, or in various stages of research or clinical trials.

Furthermore, depending on the user in question, the distinction between formulations may be critical, or it may be trivial, and therefore serving the needs of all users is a challenge. For example, a formulation chemist considers the properties of a salt formulation that differs from the active ingredient alone, such as, changes in solubility, stability, hygroscopicity (i.e., the capacity of a formulation to react to the moisture content of the air by absorbing or releasing water vapor) and other factors. Therefore, the distinction between montelukast and montelukast sodium, for example, is very important to the formulation chemist. In contrast, a medicinal chemist working in the discovery phase of drug development is concerned primarily with finding a chemical that will bind to its intended protein target. For that medicinal chemist, the differences between formulations is immaterial and montelukast and montelukast sodium are effectively the same.

Further complicating this distinction is the fact that while brand names for drugs can only accurately refer to a single formulation, since the brand names are specifically licensed and regulated products, the use of brand names in conversation, documentation or other literature is often inconsistent. For example, while montelukast sodium has a specific brand name, the brand name may be used in various text references to describe either the active ingredient or the formulation, sometimes interchangeably.

Existing chemical databases and software services have failed to present a solution for addressing these differing needs. Chemical information products usually serve only a single perspective, most often the one in which formulations are unimportant, and group all formulations of a compound together as a single record in a chemical database. However, even with this more limited scope these existing platforms often do not accurately represent a single perspective, containing inconsistencies such as grouping montelukast and montelukast sodium together, while maintaining separate records for imatinib and imatinib mesylate.

Therefore, it may be advantageous to, among other things, present a cognitive computing-based solution to simultaneously serve the interests of both user perspectives. This invention presents a system and method for identifying and storing chemical compounds with representation, which is aware of nuances in chemical formulation and can treat them separately or together as any user requires.

According to at least one embodiment, the automated classification and chemical formulation program may include a data processing pipeline in which at least one source data is received, at least one chemical compound is identified (i.e., named entity recognition phase), at least one structure representation of the chemical compound is assigned (i.e., named entity resolution phase), at least one unformulated representation of the chemical compound is computed (i.e., chemical formulation and composition interpretation phase), and the structure representation and unformulated representation of the chemical compound is indexed and stored in a cognitive search and analytics database (i.e., data indexing phase). The data processed by the data processing pipeline may then be accessed, searched and queried based on a request by a user (i.e., search and analytics phase).

According to at least one embodiment, the automated classification and chemical formulation program may include an automated generation of unformulated representations for compounds that includes the automated removal, if necessary, of salts, associated charges and other specific nuances of the constituent atoms, and bonds of a structure representation of a compound provided as either a formulation or an active ingredient only. The present embodiment may include the indexing or other storage of these unformulated representations, together with or separately from the storage of the structure representations, with or without some manner of direct linkage between them and in such a manner to enable downstream analytics to be performed on one format or the other based on the user interest or request.

According to at least one embodiment, the automated classification and chemical formulation program may include a cognitive search and analytics system that satisfies both key perspectives of chemistry-focused users, by simultaneously a) being as precise or specific as possible in the structure representation of compounds, and b) maintaining unformulated representations of each compound that facilitate the more general search and analytics use cases for which this greater precision and granularity is not necessary.

According to at least one embodiment, the automated classification and chemical formulation program may also offer the advantage of being able to serve the diverse purposes of both the medicinal chemist in early drug discovery and the formulation chemist in later drug development, while existing chemical databases and software products cater to only one perspective, and/or are inconsistent in their handling of the data.

According to at least one embodiment, the automated classification and chemical formulation program may include a cognitive data analytics workflow based at least in part upon unstructured text analytics. The present embodiment may also include the interpretation, storage and querying of structure representations (i.e., precise structure representations) versus unformulated representations (i.e., simplified structure representations) in whichever broad context they are encountered, of which the unstructured text analytics context is one example.

According to at least one embodiment, the automated classification and chemical formulation program may include a named entity recognition phase (i.e., annotation phase), which may concern the identification of compounds from source data, for instance through application of one or more natural language processing techniques to one or more sources of unstructured text information. The output of this phase may constitute a form of data representation comprising records of chemical compounds encountered in the source data, each comprising for example, information about the source document, the location in the text, the word or phrase constituting the chemical compound in question, and surrounding context.

According to at least one embodiment, the automated classification and chemical formulation program may include a named entity resolution phase that addresses the specification of the chemical structure of each chemical compound identified in the previous stage, and may comprise, for example, cross-reference to other data sources such as expert curated data, or application of cheminformatics software tools commonly known as "name-to-structure" to convert the text information into a structure representation, such as a simplified molecular-input line-entry system (SMILES) string, the IUPAC International Chemical Identifier (InChI™), or other such methods and representation formats. In the named entity resolution phase any candidate compound previously identified may be rejected if no structure can be successfully or unambiguously generated. The named entity resolution phase may be assigned the most specific chemical compound representation possible based on the provided data (e.g., to include formulation data).

According to at least one embodiment, the automated classification and chemical formulation program may include a chemical formulation and composition interpretation phase in which the structure representation provided by the named entity resolution phase, including any formulation information, may be utilized to automatically generate an unformulated representation. Each structure representation may be utilized to generate one or more unformulated representations, depending on the implementation details (i.e., specific direction by an administrator or user on how to generate the unformulated representation), and may include the possibility that the computed unformulated representation may be identical to the input structure representation, for instance if the simplification actions have no effect on the input structure representation.

According to at least one embodiment, the automated classification and chemical formulation program may include a data indexing phase in which the structure representations, as well as the unformulated representations, may be indexed or otherwise stored in a medium for search, querying and other analytics as required by the broader context (e.g., the unstructured text analytics context). The records generated in the data indexing phase may be stored together as a single record comprising multiple fields (e.g., general information on the compound associated with the record), or separately with or without a direct linkage or other association (e.g., associated groups of chemical compounds) between each record. The stored data may comprise a reference to the original source of each chemical compound as determined by the downstream analytics applications within the broader context of the present embodiment. As an example, a single compound mined from a single document may, at the data indexing phase in the embodiment described herein, be reflected in two distinct data records, one each for the structure representation and unformulated representation, differing only by the structure representation (i.e., with the source document), and possibly also by the span of text in question, and reflecting the common provenance of the two representations of the subject compound.

According to at least one embodiment, the automated classification and chemical formulation program may include a search and analytics phase. In the search and analytics phase, the data previously computed and stored may be accessed, searched and queried as requested by the user. A user may, for example, analyze on all precise compound data (i.e., compound data associated with the structure representation) across some set of source documents, and equivalently upon all simplified compound data (i.e., compound data associated with the unformulated representation) across some set of source documents. For example, the user may input a compound such as montelukast sodium, and choose for the system to understand the input precisely as such, or in the unformulated form of montelukast alone. Furthermore, the user may then perform a search for unstructured text documents mentioning chemicals that are structurally related to their input, requesting the results itemized by either structure representation, such that documents mentioning e.g., imatinib and imatinib mesylate comprise separate results items, or itemized by unformulated representation, such that documents mentioning e.g., imatinib and imatinib mesylate are combined into a single results item.

According to at least one embodiment, the automated classification and chemical formulation program may be utilized for combination treatments in which the drug products comprise more than one active ingredient. For example, Zestoretic® (i.e., generic name is Hydrochlorothiazide and Lisinopril) (Zestoretic® and all Zestoretic®-based trademarks and logos are trademarks or registered trademarks of Imperial Chemical Industries PLC and/or its affiliates) is a combination treatment for angiotensin converting enzyme (ACE) inhibitor and a diuretic used to treat hypertension that includes two active ingredients, Hydrochlorothiazide and Lisinopril. The removal of either of the active ingredients in the simplification stage may be undesirable. Therefore, the compound comparison step (e.g., based on molecular weight) may differentiate the active ingredients and other components, even when there is more than one of either type. Accordingly, Zestoretic® would be unchanged as a result of simplification, whereas a formulation of Zestoretic®, such as Zestoretic hydrochloride would be unformulated to Zestoretic®. Using the SMILES notation:
Zestoretic® (Hydrochlorothiazide and Lisinopril):
NS(=O)(=O)c1cc2c(NCNS2(=O)=O)cc1C1.NCCCC[C@H](N[C@@H](CCc1ccccc1)C(P)=O)C (=O)N1CCC[C@H]1C(O)=O
Of the form "A.B"
Zestoretic® Sodium:
[Na].NS(=O)(=O)c1cc2c(NCNS2(=O)=O)cc1C1.NCCCC[C@H](N[C@@H](CCc1ccccc1)C(O)=O)C(=O)N1CCC[C@H]1C(O)=O
Of the form "C.A.B"
Unformulated or Simplified form of each:
NS(=O)(=O)c1cc2c(NCNS2(=O)=O)cc1C1.NCCCC[C@H](N[C @ @H](CCc1ccccc1)C(O)=O)C (=O)N1CCC[C@H]1C(O)=O
Of the form "A.B"

According to at least one embodiment, the automated classification and chemical formulation program may include the ability to delimit, interpret and compare the constituent components of structure representations, in order to generate unformulated forms based upon the precise forms entered as input. For example, Drug XY is a generic name for a target therapy that is interpreted as comprising two distinct components, X and Y, in which the analysis of each compound formulation can take place independently of each other. These two components of Drug XY may be compared in terms of various metrics of structure representation, and the order in the SMILES or other notations. In addition, the molecular weight of the two components can be compared directly, and the automatic conclusion is that the Y in Drug XY is of significantly lower mass than the X in Drug XY. Therefore, X is the primary ingredient of interest, and an unformulated representation of Drug XY may be computed by simply removing the "Y" component, leaving only the "X" component (i.e., the unformulated form of Drug XY is "X"). As such, the input of X produces an identical output. Therefore, the two differing formulations, comprising two different structure representations, would map to the same unformulated representation. Accordingly, in the present embodiment of the automated classification and chemical formulation program as exemplified by another drug discovery generator (e.g., Watson for Drug Discovery™, Watson for Drug Discovery and all Watson for Drug Discovery-based trademarks and logos are trademarks or registered trademarks of International Business Machines Corporation and/or its affiliates), a user may search for "X" and recover a set of documentary evidence in which X is mentioned. The user may search "Drug XY" and recover a set of documentary evidence in which Drug XY is mentioned, and the user may also search "All formulations of X"

and recover a set of documentary evidence which mentions any compound whose structure representation may be unformulated to X, comprising X itself, Drug XY, and possibly other formulations not known in advance to the user but which the automated classification and chemical formulation program automatically discovers to be formulations of X such as "XZ" or "XW".

The present embodiment may include a formulation-aware cognitive search capability that demonstrates the intrinsic extensibility of the automated classification and chemical formulation program to future formulations of existing or new drugs as a drug enters the market, is discussed in the literature, or enters the public domain without the need to supply additional expert data or training to the system.

The present embodiment may further perform other simplifying actions, such as charge removal, which is sometimes necessary to more completely simplify the structure representation of a formulation. For example, in some cases, a more precise structure representation of a formulation is achievable, where the chemical association between the components is represented more explicitly than by simply concatenating delimited components. Using SMILES notation, consider benzene and benzenium:
Benzene:
c1cccc1
Benzenium:
c1cc[cH+]cc1
Unformulated form of each:
c1cccc1

In the previous example, in the SMILES for benzene, the carbon atom has no charge ("C"), and the compound overall has a neutral charge as is commonplace. However, in the SMILES for benzenium, this carbon atom has a positive charge ("[cH+]"). As such, the automated classification and chemical formulation program may compute the unformulated representation of benzenium to be the structure of benzene, through a two-step process comprising: 1) the identification, separation and comparison of any constituent components and identification of the active ingredient, as in the Zestoretic® example, however in this example this step has no effect since both structure representations comprise only a single component; and 2) the removal or neutralization of any charge on the active ingredient.

According to at least one embodiment, the automated classification and chemical formulation program may satisfy both chemistry user perspectives by allowing for different, chemically-aware levels of search granularity as each user requests.

Referring to FIG. 1, an exemplary networked computer environment 100 in accordance with one embodiment is depicted. The networked computer environment 100 may include a computer 102 with a processor 104 and a data storage device 106 that is enabled to run a software program 108 and an automated classification and chemical formulation program 110a. The networked computer environment 100 may also include a server 112 that is enabled to run an automated classification and chemical formulation program 110b that may interact with a database 114 and a communication network 116. The networked computer environment 100 may include a plurality of computers 102 and servers 112, only one of which is shown. The communication network 116 may include various types of communication networks, such as a wide area network (WAN), local area network (LAN), a telecommunication network, a wireless network, a public switched network and/or a satellite network. It should be appreciated that FIG. 1 provides only an illustration of one implementation and does not imply any limitations with regard to the environments in which different embodiments may be implemented. Many modifications to the depicted environments may be made based on design and implementation requirements.

The client computer 102 may communicate with the server computer 112 via the communications network 116. The communications network 116 may include connections, such as wire, wireless communication links, or fiber optic cables. As will be discussed with reference to FIG. 3, server computer 112 may include internal components 902a and external components 904a, respectively, and client computer 102 may include internal components 902b and external components 904b, respectively. Server computer 112 may also operate in a cloud computing service model, such as Software as a Service (SaaS), Analytics as a Service (AaaS), Platform as a Service (PaaS), or Infrastructure as a Service (IaaS). Server 112 may also be located in a cloud computing deployment model, such as a private cloud, community cloud, public cloud, or hybrid cloud. Client computer 102 may be, for example, a mobile device, a telephone, a personal digital assistant, a netbook, a laptop computer, a tablet computer, a desktop computer, or any type of computing devices capable of running a program, accessing a network, and accessing a database 114. According to various implementations of the present embodiment, the automated classification and chemical formulation program 110a, 110b may interact with a database 114 that may be embedded in various storage devices, such as, but not limited to a computer/mobile device 102, a networked server 112, or a cloud storage service.

According to the present embodiment, a user using a client computer 102 or a server computer 112 may use the automated classification and chemical formulation program 110a, 110b (respectively) to utilize an automated classification and formulation-aware search and analytics of at least one chemical compound to generate and store at least one specific structure representation for a plurality of chemical compounds. The automated classification and chemical formulation method is explained in more detail below with respect to FIG. 2.

Figure 2:
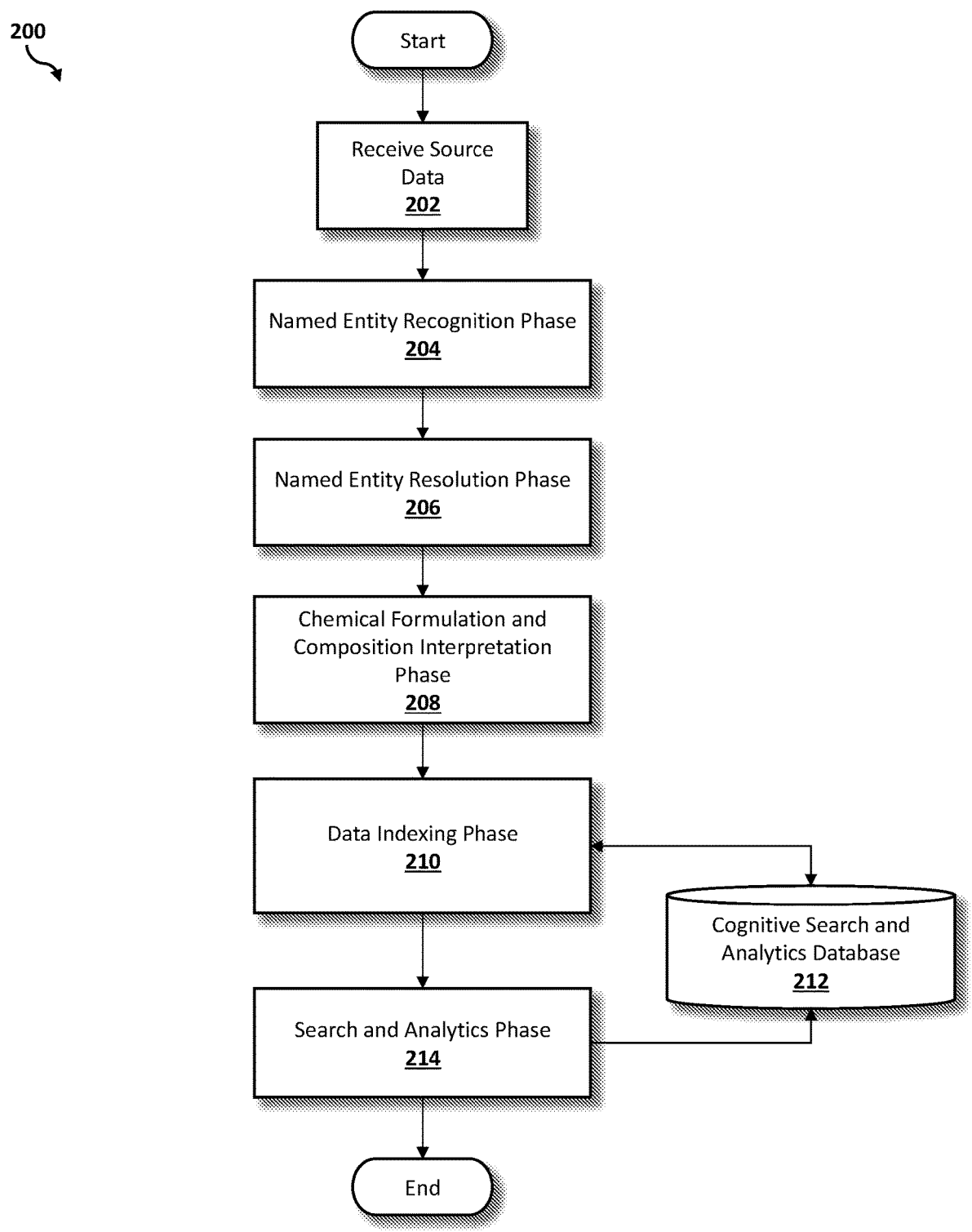
FIG. 2 is an operational flowchart illustrating a process for utilizing an automated classification and formulation-aware search and analytics of at least one chemical compound to generate and store at least one representation for a plurality of chemical compounds according to at least one embodiment.

Referring now to FIG. 2, an operational flowchart illustrating the exemplary automated classification and chemical formulation process 200 to generate and store at least one specific structure representation for a plurality of chemical compounds from at least one chemical compound used by the automated classification and chemical formulation program 110a, 110b according to at least one embodiment is depicted.

At 202, at least one set of source data is received. Using a software program 108 on the user device (e.g., user's computer 102), the automated classification and chemical formulation program 110a, 110b may load (i.e., pull or retrieve) at least one set of source data as input from the server 112 or a cloud storage service via communications network 116. The source data (i.e., unstructured text sources) may include documents (e.g., medical or scientific abstracts, full text scientific articles, full text patents, clinical trial reports, drug labels, medical or scientific literature), and secondary internet sources. Alternatively, the user may manually upload the at least one set of source data, without the use of the server 112 or a cloud storage service.

For example, a drug research facility utilizes the automated classification and chemical formulation program 110a, 110b to identify and store the chemical compounds for drugs associated with cancer treatment and therapy. The automated classification and chemical formulation program 110a, 110b utilizes an automated software program to search a list of pre-approved medical and scientific literature and websites for recent scientific publications associated with advancements on drug and therapy treatments for patients diagnosed with cancer. The automated software program discovered ten different scientific publications. Each of the scientific publications are uploaded into the automated classification and chemical formulation program 110a, 110b, as well as stored in a local cloud storage associated with the drug research facility.

In another embodiment, the automated classification and chemical formulation program 110a, 110b may prompt the user (e.g., via dialog box) to provide details or parameters that may customize the source data by limiting the type of source data uploaded. Once the user starts the automated classification and chemical formulation program 110a, 110b, the user may be prompted (e.g., via dialog box) to indicate whether the user has any parameters or details to customize the source data. The dialog box may include a list of possible parameters (e.g., active ingredient, usage). The user may then click on the button located, for example, to the left of the possible parameters, which may expand the dialog box, and the user may be prompted (e.g., via the same dialog box) to provide details related to the selected parameters. The dialog box may expand and prompt the user to confirm the selected parameter and provided details by clicking the "Yes" or "No" buttons under a statement restating the selected parameter and provided details. Once the user clicks "Yes," the dialog box may disappear. If, however, the user selects the "No" button, then the dialog box may remain for the user to clarify the selected parameters and provided details.

Then, at 204, the named entity recognition phase is commenced. In the named entity recognition phase (i.e., annotation phase), the automated classification and chemical formulation program 110a, 110b may utilize a software program 108 (e.g., an application of one or more natural language processing techniques) on the user device (e.g., user's computer 102) for the identification of one or more chemical compounds from one or more sources of unstructured text information. The automated classification and chemical formulation program 110a, 110b may utilize a known engine to parse through the unstructured text for chemical compounds. The output of the named entity recognition phase may constitute a form of data representation including records of chemical compounds encountered in the source data (e.g., information about the source document (i.e., one or more documents in which the at least one set of source data was derived from), the location in the text, the word or phrase representing the chemical compound in question, and surrounding context). In the context of a natural language processing-based embodiment, the named entity recognition phase may be considered as the annotation phase.

In the present embodiment, the user may provide feedback after the named entity recognition phase on the validity of the output generated by the automated classification and chemical formulation program 110a, 110b, such as the word or phrase representing the chemical compound in question, and information pertaining to the source data. The user feedback may be utilized to improve the development of the automated classification and chemical formulation program 110a, 110b. As such, the next time that the data processing pipeline is executed, the named entity recognition phase may act differently for one, some or all chemical compounds based on the received feedback by the user (i.e., user feedback).

A user may provide feedback by clicking on the "User Feedback" button displayed on the bottom of the monitor associated with the user device. The user may, for example, be prompted (e.g., via first dialog box) to select the phase which the user feedback pertains to. Then, the user may be prompted (e.g., via second dialog box) to enter in a text box, in natural language, the user feedback to specific items or output related to the selected phase of the automated classification and chemical formulation program 110a, 110b. Then, the user may click the "Submit" button located at the bottom of the second dialog box. The second dialog box may then disappear.

Continuing the previous example, the automated classification and chemical formulation program 110a, 110b parses through the ten recent scientific publications for any chemical compounds associated with drugs and therapy for patients diagnosed with cancer. After searching through the ten uploaded scientific publications, the automated classification and chemical formulation program 110a, 110b identifies several chemical compounds, including Gleevec® (Gleevec® and all Gleevec®-based trademarks and logos are trademarks or registered trademarks of Novartis AG Corporation and/or its affiliates).

Then, at 206, the named entity resolution phase is commenced. During the named entity resolution phase, the automated classification and chemical formulation program 110a, 110b may utilize a software program 108 on the user device (e.g., user's computer 102) for assigning one or more precise structure information (e.g., most specific chemical compound representation possible based on the provided source data) including formulation data for each chemical compound. The structure representation (i.e., precise structure representation) may be considered the most accurate representation of the chemical structure achievable for the compound in question, including any constituent formulation information, within the constraints (i.e., two-dimensional structure representations) of the embodiment and intended usage. For example, imatinib mesylate is the chemical structure of the active ingredient imatinib, including all of its stereochemistry, charges and so on, and including the formulation details (i.e. the mesylate salt) as a separate compound within the structure representation.

The automated classification and chemical formulation program 110a, 110b may then identify the specification of a chemical structure of each chemical compound that may have been identified in the previous named entity recognition phase at 204, and may then utilize a search engine to cross-reference other data sources (e.g., expert curated data, application of cheminformatics software tools commonly known as "name-to-structure") to identify a chemical formulation for the identified chemical compound. During the named entity resolution phase, the unstructured text information, along with the identified chemical formulation, associated with at least one chemical compound from the at least one set of source data may be converted into a structure representation (e.g., a simplified molecular-input line-entry system (SMILES) string, or the IUPAC International Chemical Identifier (InChI™)).

In the present embodiment, the automated classification and chemical formulation program 110a, 110b may, during the named entity resolution phase, reject a previously identified candidate compound if no structure may be successfully or unambiguously generated. The automated classification and chemical formulation program 110a, 110b may be presented with an error message further indicating that no structure may be successfully or unambiguously generated.

Continuing the previous example, the automated classification and chemical formulation program 110a, 110b utilizes a medical search engine to gather unstructured text information and a chemical formulation associated with Gleevec®. The chemical formulation of Gleevec® includes imatinib mesylate, and imatinib mesylate has the following SMILES notation:
CS(O)(=O)=OCN1CCN(Cc2ccc(cc2)C(=O)Nc2ccc(C)c(Nc3nccc(n3)-c3cccnc3)c2)CC1
Of the form "B.A"

Then, at 208, the chemical formulation and composition interpretation phase is commenced. During the chemical formulation and composition interpretation phase, the automated classification and chemical formulation program 110a, 110b may utilize a software program 108 on the user device (e.g., user's computer 102) for computing one or more unformulated representations (i.e., unformulated representation) (e.g., without formulation, without charge, etc.) from a structure representation for each chemical compound. The one or more unformulated representations may be considered the product of removing the formulation details and other specifics included in the structure representation to include the active ingredient only. Each structure representation provided by the named entity resolution phase, including any formulation information, may be utilized to automatically generate one or more unformulated representations.

In at least one embodiment, to compute the unformulated representation of a chemical compound, the automated classification and chemical formulation program 110a, 110b may implement a two-step process. The automated classification and chemical formulation program 110a, 110b may first separate and compare the constituent components (e.g., constituent atoms and bonds) to identify the one or more active ingredients associated with the chemical compound. The automated classification and chemical formulation program 110a, 110b may then remove or neutralize any charge associated with the active ingredient.

In at least one embodiment, the generation of the unformulated representation, during the chemical formulation and composition interpretation phase, may include the identification and removal of salts from the structure representation. For example, the mesylate salt will be identified and removed from imatinib mesylate compound in which the mesylate salt is a part of the ingredients. In another embodiment, the salts may be identified by calculating and comparing the masses of the distinct molecular fragments in a composition. Therefore, the active ingredients of the chemical compound, excluding the salt molecules in the chemical compound, may be identified.

In at least one embodiment, the generation of the unformulated representation, during the chemical formulation and composition interpretation phase, may include the identification and removal of charges on constituent atoms in the structure representation.

Depending on the specific structure representation identified in the received at least one set of source data, the automated classification and chemical formulation program 110a, 110b may automatically determine whether the identification and removal of salts, charges on constituent atoms, or both, in the structure representation is necessary.

Continuing the previous example, the automated classification and chemical formulation program 110a, 110b determines that imatinib is an active ingredient in Gleevec®. The SMILES notation for imatinib is as follows:
CN1CCN(Cc2ccc(cc2)C(=O)Nc2ccc(C)c(Nc3nccc(n3)-c3cccnc3)c2)CC1
Of the form "A"

Continuing the previous example, the SMILES notation of imatinib mesylate comprises a text string of the form "B.A". The component "A" is shared between the each of the SMILES representations for imatinib mesylate and imatinib. The automated classification and chemical formulation program 110a, 110b determines that the imatinib mesylate differs only by the prepended components "B" (in this case, "CS(O)(=O)=O"), representing the mesylate, and ".", a delimiter separating the constituent components of this formulation. Additionally, imatinib mesylate is interpreted as comprising two distinct components, A and B. These two components of imatinib mesylate were compared in terms of various metrics of chemical structure representation, such as, comparing the molecular weight of the two components directly, and the automated classification and chemical formulation program 110a, 110b determined that mesylate is of significantly lower mass than the imatinib, and that therefore imatinib is the primary ingredient of interest, and a unformulated representation of imatinib mesylate can therefore be computed by simply removing or neutralizing the "B" component and the "." delimiter, leaving only the "A" component. As such, the unformulated form of imatinib mesylate is "A", (i.e., imatinib itself). In a similar manner, the unformulated or simplified version of imatinib alone will be found to also constitute "A" (i.e., imatinib).

Additionally, if the automated classification and chemical formulation program 110a, 110b determines that constituent components, salts or charges are present within the active ingredient, then the automated classification and chemical formulation program 110a, 110b will remove or neutralize these constituent components, salts or charges. In the above example with imatinib mesylate and imatinib, constituent components, salts or charges were not present and as such, the removal of these items is unnecessary by the automated classification and chemical formulation program 110a, 110b. Therefore, the structure representation for imatinib constitutes the unformulated representation for Gleevec®.

In another embodiment, the automated classification and chemical formulation program 110a, 110b may include the possibility that the computed unformulated representation, generated during the chemical formulation and composition interpretation phase at 208, may be identical to the input structure representation. The unformulated form of aspirin, for example, is identical to the structure representation of aspirin. During the chemical formulation and composition interpretation phase, the automated classification and chemical formulation program 110a, 110b may determine that there are no further simplifying actions that may be taken on the structure representation, since the structure representation is already in the simplest form. As such, the user may be presented with a message indicating that the computed unformulated representation and structure representations are identical. Alternatively, for aspirin sodium (i.e., a salted form of aspirin), the automated classification and chemical formulation program 110a, 110b will be further unformulated to aspirin, thereby removing the salts to generate an unformulated representation. Therefore, aspirin and aspirin sodium may have the same unformulated representation.

In another embodiment, distinct or additional simplification actions may be encoded into the chemical formulation and composition interpretation phase to generate a distinct unformulated representation associated with a chemical compound. For example, if "removal of hydrate groups" is defined as a new simplification action, then the unformulated representation associated with aspirin will be different from the structure representation associated with aspirin since aspirin includes one hydrate group. The removal of that hydrate group may change the representation of aspirin, and therefore, the unformulated representation and structure representation will no longer be identical.

The automated classification and chemical formulation program 110a, 110b may encode new or distinct simplification actions during the chemical formulation and composition interpretation phase. For example, "removal of hydrate groups" can be defined as a simplification action.

Then, at 210, the data indexing phase is commenced. During the data indexing phase, the automated classification and chemical formulation program 110a, 110b may utilize a software program 108 on the user device (e.g., user's computer 102) for indexing and storing the structure representation and unformulated representation associated with the received at least one set of source data (e.g., distinct but linked record types) in a cognitive search and analytics database 212 (e.g., database 114) for searching, querying and analyzing by a broader context (e.g., unstructured text analytics context). The structure representation and unformulated representation may be stored separately as single records. As such, each annotated chemical compound generated (or mined) from the received at least one set of source data may produce two stored records (i.e., one record associated with the structure representation, and another record associated with the unformulated representation) with or without a direct linkage or other association (e.g., other chemical compounds included with the same group) between each of the records. The stored data may include a reference to the original source of each chemical compound as necessary for a downstream analytics application within the broader context of the embodiment. The single chemical compound may further include a span of text in question, and reflect the common provenance of the two representations of the single chemical compound.

In the present embodiment, for chemical compounds with identical structure representation and unformulated representation, the records for each representation may be stored separately. Therefore, a search performed exclusively for a specific representation (e.g., either structure representation or unformulated representation) may return that result.

In the present embodiment, the automated classification and chemical formulation program 110a, 110b may modify the stored and indexed records on a frequent basis, whenever a data processing pipeline phase is performed or a modification or change occurs in the data processing pipeline. Depending on whether the automated classification and chemical formulation program 110a, 110b detects a change in the previous results based on the recently performed or modified data processing pipeline, the previous results may be overwritten and the new results may be stored and indexed for the user. For example, if a user provides feedback during the named entity recognition phase, the automated classification and chemical formulation program 110a, 110b may implement that feedback and therefore, change the previously generated results, thereby causing the automated classification and chemical formulation program 110a, 110b to modify the results associated with the feedback. The previous results may be overwritten by the modified results, which may be stored and indexed in the cognitive search and analytics database 212.

In at least one embodiment, the automated classification and chemical formulation program 110a, 110b may subject the results of the data processing pipeline to various stages of testing and quality assessment before the previous results are overwritten with the modified results. For instance, statistical methods can be encoded to automatically assess whether the candidate new output data differs significantly from the previous output data, such as certain chemical representations occurring much more or less frequently than previously, which may prompt a warning for human expert review before acceptance of the new data.

Continuing the previous example, the structure representation for Gleevec® (i.e., imatinib mesylate) and the unformulated representation for Gleevec® (i.e., imatinib) are indexed in separate records. Each record includes a cross-reference to the other structure representation, and a reference to the source documents that Gleevec® was identified in during the named entity recognition phase in the cognitive search and analytics database 212.

In at least one embodiment, the automated classification and chemical formulation program 110a, 110b may store and index the structure representation and unformulated representation, for each chemical compound, together as a single record thereby eliminating the apparent redundancy of separate storage for each type of representation.

In the present embodiment, the cognitive search and analytics database 212 may be a global database in which user access may be restricted. As such, the records for the structure representation or unformulated representation, associated with a chemical compound, computed by the automated classification and chemical formulation program 110a, 110b for any user may be included in the cognitive search and analytics database 212. For example, if a user provides private and confidential information regarding Drug Q that a specific research group associated with the user is testing, then the data records associated with the annotations of Drug Q may be stored with corresponding privilege information such that only users from that specific research group may access those data records.

In another embodiment, the cognitive search and analytics database 212 may include a local database, in addition to a global database. The records may be limited to an individual user or specific group associated with a user. For example, one research facility or group may have one local database. The local database may periodically store and index the generated records with the global database associated with the cognitive search and analytics database 212, which may include each record generated by all the local databases. The user may, through limited user access, retrieve records not stored and indexed on the local database, but rather only stored and indexed on a global database.

Then, at 214, the search and analytics phase is commenced. During the search and analytics phase, the automated classification and chemical formulation program 110a, 110b may utilize a software program 108 for searching and performing analytics on data records, applying to either structure representation or unformulated representation associated with at least one record based on the request of a user. The received at least one set of source data previously computed and stored may be accessed, searched, queried and analyzed during the search and analytics phase, when a request is received by the user. A user may perform analytics on all precise compound data across one or more sets of source data, and equivalently upon the unformulated compound data across one or more sets of source data.

The automated classification and chemical formulation program 110a, 110b may utilize the software program 108 on the user device (e.g., user's computer 102) to receive as input a request by the user. The request may include a name (e.g., generic name, brand name, molecular compound name) of a chemical compound or group of chemical compounds, or the structure representation of a specific chemical compound. The automated classification and chemical formulation program 110a, 110b may then search the cognitive search and analytics database 212 for the records associated with the user request. The user may utilize the automated classification and chemical formulation program 110a, 110b to query the data records that were generated offline during the data processing pipeline for information pertaining to a specific chemical compound or group of chemical compounds, including how the compound may be discussed in literature and associated text analytics, as well as to discover compounds that are structurally related to the specific chemical compound and other associated chemical structure analytics. For instance, all chemicals extracted from unstructured text may be compared to the user input and those chemicals with sufficient structural similarity to the input can be selected; the user may request that their input be handled in the precise format (i.e., associated with the structure representation) or unformulated format, and/or that the results are returned in precise or unformulated format. As such, documents within which the resulting chemicals were discovered may be returned to the user; and may involve querying the chemical records if corresponding document identifiers are stored therein as part of the embodiment, otherwise, for example, querying a secondary data indexing system, which specifically aligns chemicals with documents in which they were identified. Based on the user request, the constituent documents may be presented in a granular visualization itemized by corresponding precise or unformulated representation (e.g., results for imatinib and results for imatinib mesylate would be distinct in the former, and combined into the same results item in the latter). The results of the user request may be retrieved from the cognitive search and analytics database 212, and the automated classification and chemical formulation program 110a, 110b may then return the results to the user.

In the present embodiment, if the user request includes the actual structure of a chemical compound, rather than solely a name associated with the chemical compound or group of chemical compounds, then the automated classification and chemical formulation program 110a, 110b may interpret the input as a structure and return the records associated with that structure.

In the present embodiment, if the automated classification and chemical formulation program 110a, 110b is unable to return any results for the user request, the automated classification and chemical formulation program 110a, 110b may present an error message to the user further indicating that no results may be successfully or unambiguously generated to the user request.

In the present embodiment, if the user submits a compound that the automated classification and chemical formulation program 110a, 110b fails to understand, an error message may be displayed further indicating that the input cannot be processed. The user may then be prompted (e.g., via modal dialog box) to indicate whether the user wants assistance. If the user clicks, for example, the "Decline" button located at the bottom of the modal dialog box, then the modal dialog box may disappear. If, however, the user clicks, for example, "Accept" button located at the bottom of the modal dialog box, then the modal dialog box may expand to provide the user with a list of suggested requests (e.g., list of compounds with a similar spelling or structure representation as the user request), or provide an additional explanation as to why the user request could not be processed (e.g., the user request included an unrecognizable character) by the automated classification and chemical formulation program 110a, 110b.

Continuing the previous example, a user in the same drug research facility is performing research on pharmaceutical preparations for the use in the field of oncology. As such, the user submits a request for information pertaining to Gleevec®. The automated classification and chemical formulation program 110a, 110b then performs a cognitive search for information associated with Gleevec®. The automated classification and chemical formulation program 110a, 110b would retrieve each record related to the structure representation associated with Gleevec® (i.e., imatinib mesylate) and the unformulated representation associated with Gleevec® (i.e., imatinib). Since imatinib mesylate simplifies to imatinib, as does imatinib itself and potentially any other formulations thereof, the results of the unformulated structure search on imatinib will be equal to, or a superset of, the results of the precise structure (i.e., associated with the structure representation) search on imatinib mesylate, since the unformulated search constitutes results for all identified chemicals which simplify to imatinib, i.e., it will comprise results for imatinib, for imatinib mesylate, and so on. The automated classification and chemical formulation program 110a, 110b presents results to the user.

In the absence of the automated classification and chemical formulation program 110a, 110b, a medicinal chemist user who is interested in documentary evidence concerning any formulation of a specific drug may have to deliberately perform individual searches for each of the drug formulations, which is likely to be a very manual process highly prone to error or omission, and the medicinal chemist user may then have to consolidate the generated results. Alternatively, and again in the absence of the automated classification and chemical formulation program 110a, 110b, the formulation specifics may be ignored and all the documents may be consolidated under one large record for that specific drug. Therefore, the functionality of a computer may be improved by the automated classification and chemical formulation program 110a, 110b because the assigned unformulated representation, which is generated as an output, may be maintained to facilitate more general search and analytics use cases for which greater precision and granularity are unnecessary, while simultaneously or consecutively being as specific as possible in the search of structure representations. The automated classification and chemical formulation program 110a, 110b may satisfy multiple chemistry user perspectives by allowing a computer to perform different, chemically-aware levels of search granularity as each user requires.

It may be appreciated that FIG. 2 provides only an illustration of one embodiment and does not imply any limitations with regard to how different embodiments may be implemented. Many modifications to the depicted embodiment(s) may be made based on design and implementation requirements.

Figure 3:
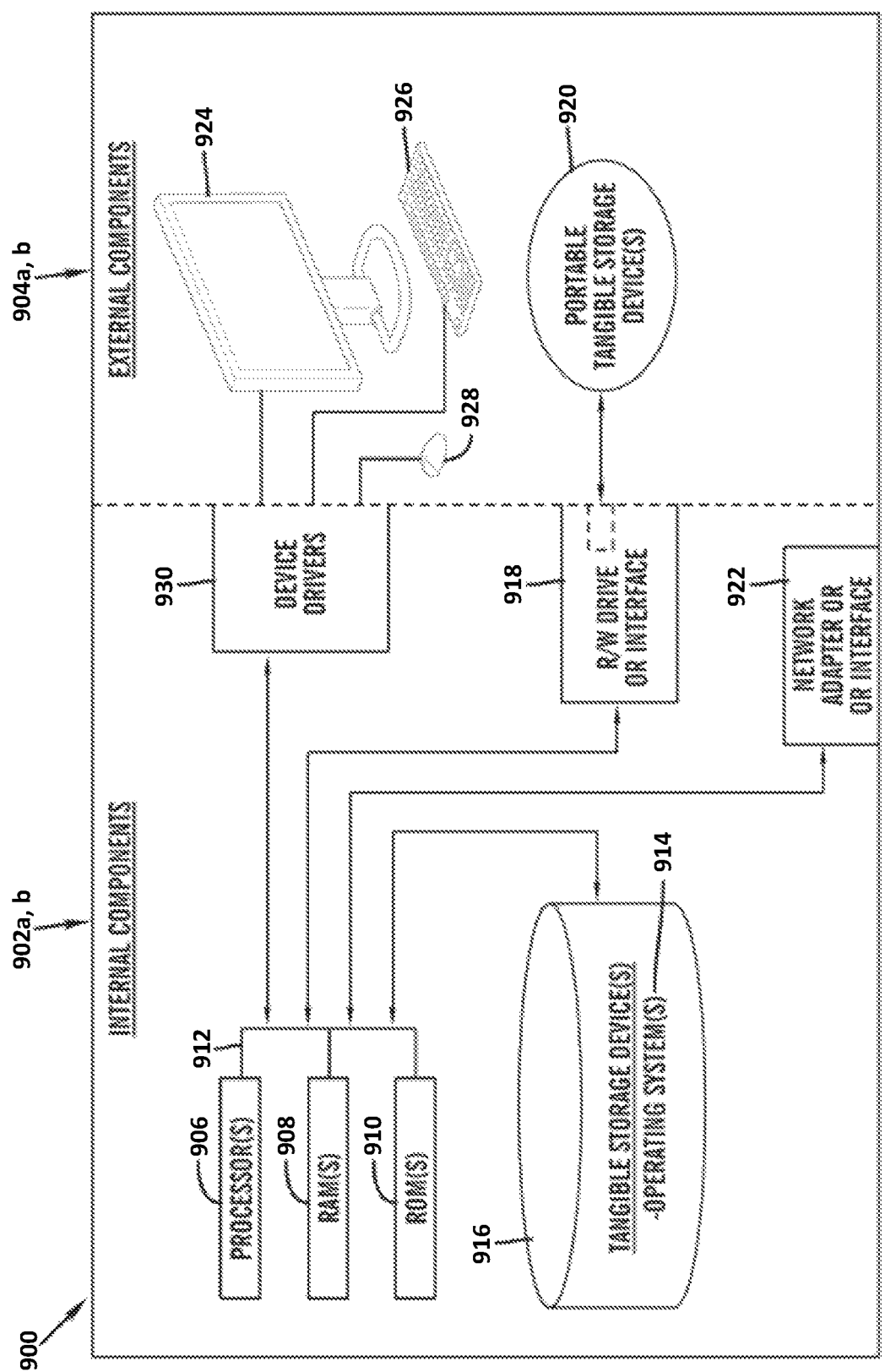
FIG. 3 is a block diagram of internal and external components of computers and servers depicted in FIG. 1 according to at least one embodiment.

FIG. 3 is a block diagram 900 of internal and external components of computers depicted in FIG. 1 in accordance with an illustrative embodiment of the present invention. It should be appreciated that FIG. 3 provides only an illustration of one implementation and does not imply any limitations with regard to the environments in which different embodiments may be implemented. Many modifications to the depicted environments may be made based on design and implementation requirements.

Data processing system 902, 904 is representative of any electronic device capable of executing machine-readable program instructions. Data processing system 902, 904 may be representative of a smart phone, a computer system, PDA, or other electronic devices. Examples of computing systems, environments, and/or configurations that may represented by data processing system 902, 904 include, but are not limited to, personal computer systems, server computer systems, thin clients, thick clients, hand-held or laptop devices, multiprocessor systems, microprocessor-based systems, network PCs, minicomputer systems, and distributed cloud computing environments that include any of the above systems or devices.

User client computer 102 and network server 112 may include respective sets of internal components 902 a, b and external components 904 a, b illustrated in FIG. 3. Each of the sets of internal components 902 a, b includes one or more processors 906, one or more computer-readable RAMs 908 and one or more computer-readable ROMs 910 on one or more buses 912, and one or more operating systems 914 and one or more computer-readable tangible storage devices 916. The one or more operating systems 914, the software program 108 and the automated classification and chemical formulation program 110a in client computer 102, and the automated classification and chemical formulation program 110b in network server 112, may be stored on one or more computer-readable tangible storage devices 916 for execution by one or more processors 906 via one or more RAMs 908 (which typically include cache memory). In the embodiment illustrated in FIG. 3, each of the computer-readable tangible storage devices 916 is a magnetic disk storage device of an internal hard drive. Alternatively, each of the computer-readable tangible storage devices 916 is a semiconductor storage device such as ROM 910, EPROM, flash memory or any other computer-readable tangible storage device that can store a computer program and digital information.

Each set of internal components 902 a, b also includes a R/W drive or interface 918 to read from and write to one or more portable computer-readable tangible storage devices 920 such as a CD-ROM, DVD, memory stick, magnetic tape, magnetic disk, optical disk or semiconductor storage device. A software program, such as the software program 108 and the automated classification and chemical formulation program 110a, 110b can be stored on one or more of the respective portable computer-readable tangible storage devices 920, read via the respective R/W drive or interface 918 and loaded into the respective hard drive 916.

Each set of internal components 902 a, b may also include network adapters (or switch port cards) or interfaces 922 such as a TCP/IP adapter cards, wireless Wi-Fi interface cards, or 3G or 4G wireless interface cards or other wired or wireless communication links. The software program 108 and the automated classification and chemical formulation program 110a in client computer 102 and the automated classification and chemical formulation program 110b in network server computer 112 can be downloaded from an external computer (e.g., server) via a network (for example, the Internet, a local area network or other, wide area network) and respective network adapters or interfaces 922. From the network adapters (or switch port adaptors) or interfaces 922, the software program 108 and the automated classification and chemical formulation program 110a in client computer 102 and the automated classification and chemical formulation program 110b in network server computer 112 are loaded into the respective hard drive 916. The network may comprise copper wires, optical fibers, wireless transmission, routers, firewalls, switches, gateway computers and/or edge servers.

Each of the sets of external components 904 a, b can include a computer display monitor 924, a keyboard 926, and a computer mouse 928. External components 904 a, b can also include touch screens, virtual keyboards, touch pads, pointing devices, and other human interface devices.

Each of the sets of internal components 902 a, b also includes device drivers 930 to interface to computer display monitor 924, keyboard 926 and computer mouse 928. The device drivers 930, R/W drive or interface 918 and network adapter or interface 922 comprise hardware and software (stored in storage device 916 and/or ROM 910).

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider.

The consumer does not manage or control the underlying cloud infrastructure including networks, servers, operating systems, or storage, but has control over the deployed applications and possibly application hosting environment configurations.

Analytics as a Service (AaaS): the capability provided to the consumer is to use web-based or cloud-based networks (i.e., infrastructure) to access an analytics platform. Analytics platforms may include access to analytics software resources or may include access to relevant databases, corpora, servers, operating systems or storage. The consumer does not manage or control the underlying web-based or cloud-based infrastructure including databases, corpora, servers, operating systems or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 4:
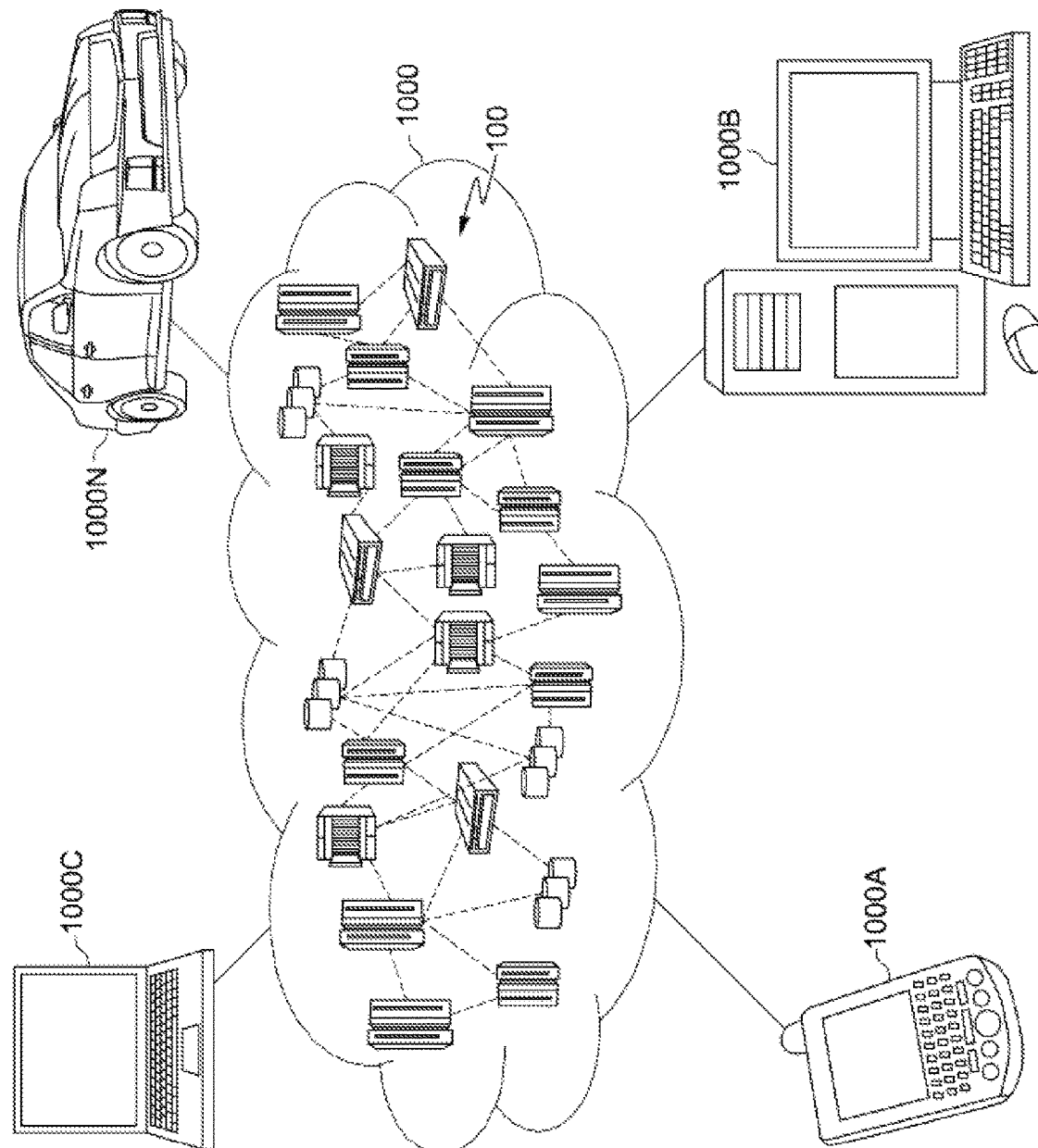
FIG. 4 is a block diagram of an illustrative cloud computing environment including the computer system depicted in FIG. 1, in accordance with an embodiment of the present disclosure.

Referring now to FIG. 4, illustrative cloud computing environment 1000 is depicted. As shown, cloud computing environment 1000 comprises one or more cloud computing nodes 100 with which local computing devices used by cloud consumers, such as, for example, personal digital assistant (PDA) or cellular telephone 1000A, desktop computer 1000B, laptop computer 1000C, and/or automobile computer system 1000N may communicate. Nodes 100 may communicate with one another. They may be grouped (not shown) physically or virtually, in one or more networks, such as Private, Community, Public, or Hybrid clouds as described hereinabove, or a combination thereof. This allows cloud computing environment 1000 to offer infrastructure, platforms and/or software as services for which a cloud consumer does not need to maintain resources on a local computing device. It is understood that the types of computing devices 1000A-N shown in FIG. 4 are intended to be illustrative only and that computing nodes 100 and cloud computing environment 1000 can communicate with any type of computerized device over any type of network and/or network addressable connection (e.g., using a web browser).

Figure 5:
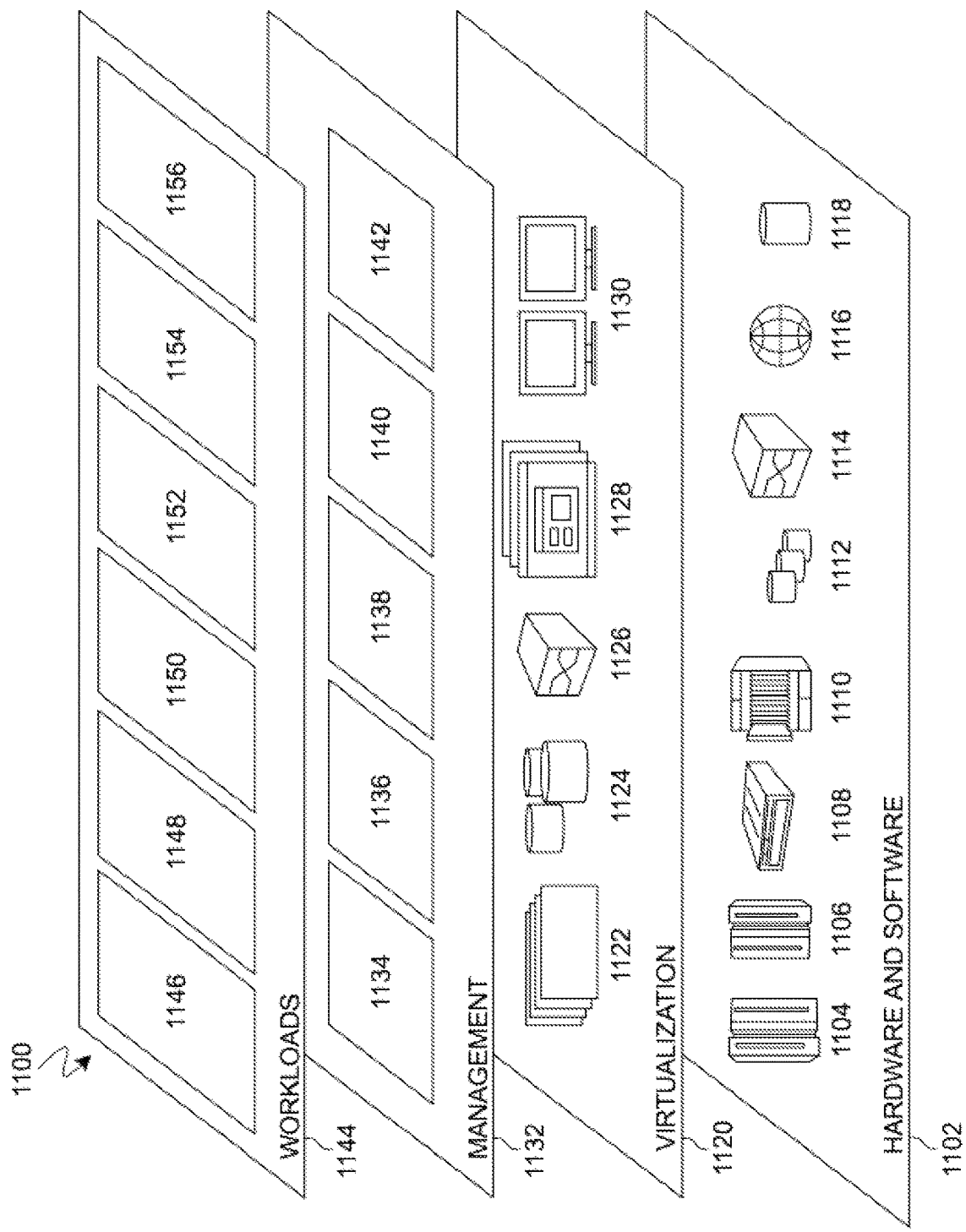
FIG. 5 is a block diagram of functional layers of the illustrative cloud computing environment of FIG. 4, in accordance with an embodiment of the present disclosure.

Referring now to FIG. 5, a set of functional abstraction layers 1100 provided by cloud computing environment 1000 is shown. It should be understood in advance that the components, layers, and functions shown in FIG. 5 are intended to be illustrative only and embodiments of the invention are not limited thereto. As depicted, the following layers and corresponding functions are provided:

Hardware and software layer 1102 includes hardware and software components. Examples of hardware components include: mainframes 1104; RISC (Reduced Instruction Set Computer) architecture based servers 1106; servers 1108; blade servers 1110; storage devices 1112; and networks and networking components 1114. In some embodiments, software components include network application server software 1116 and database software 1118.

Virtualization layer 1120 provides an abstraction layer from which the following examples of virtual entities may be provided: virtual servers 1122; virtual storage 1124; virtual networks 1126, including virtual private networks; virtual applications and operating systems 1128; and virtual clients 1130.

In one example, management layer 1132 may provide the functions described below. Resource provisioning 1134 provides dynamic procurement of computing resources and other resources that are utilized to perform tasks within the cloud computing environment. Metering and Pricing 1136 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 1138 provides access to the cloud computing environment for consumers and system administrators. Service level management 1140 provides cloud computing resource allocation and management such that required service levels are met. Service Level Agreement (SLA) planning and fulfillment 1142 provide pre-arrangement for, and procurement of, cloud computing resources for which a future requirement is anticipated in accordance with an SLA.

Workloads layer 1144 provides examples of functionality for which the cloud computing environment may be utilized. Examples of workloads and functions which may be provided from this layer include: mapping and navigation 1146; software development and lifecycle management 1148; virtual classroom education delivery 1150; data analytics processing 1152; transaction processing 1154; and automated classification and chemical formulation 1156. An automated classification and chemical formulation program 110a, 110b provides a way to perform an automated classification and chemical formulation of at least one chemical compound to generate and store at least one representation for a plurality of chemical compounds.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for identifying and storing at least one representation to at least one chemical compound, the method comprising:
   identifying at least one chemical compound associated with at least one set of source data, wherein the source data comprises an unstructured text;
   comparing a plurality of data sources associated with the identified at least one chemical compound;
   converting the at least one set of source data into at least one structure representation based on the compared plurality of data sources and one or more applications of cheminformatics software tools that convert the at least one chemical compound into an identifier chemical formulation or a simplified molecular-input line-entry system string;
   assigning the at least one structure representation to the identified at least one chemical compound associated with the at least one set of source data;
   computing one or more unformulated representations based on the assigned at least one structure representation, by identifying one or more active ingredients and neutralizing one or more charges associated with the one or more active ingredients;
   indexing the computed one or more unformulated representations and the assigned at least one structure representation;
   storing the indexed one or more unformulated representations and the indexed at least one structure representation separately as a single record in a cognitive search and analytics database; and
   in response to a determination that the assigned at least one structure representation includes a plurality of salts, removing the plurality of salts associated with the assigned at least one structure representation.

2. The method of claim 1, further comprising:
   receiving a request by a user;
   querying the cognitive search and analytics database based on the received request; and
   in response to retrieving one or more results to the received request from the cognitive search and analytics database, returning the one or more results to the received request to the user.

3. The method of claim 2 in which the received request includes at least one of the following:
   at least one chemical compound;
   at least one group of chemical compounds; or
   at least one structure representation associated with a chemical compound or group of chemical compounds.

4. The method of claim 1 in which the at least one set of source data further includes one or more sources of secondary internet sources.

5. The method of claim 1, wherein identifying at least one chemical compound associated with at least one set of source data, further comprises:
   generating a form of data representation, wherein the generated data representation includes at least one record of at least one chemical compound associated with the at least one set of source data.

6. The method of claim 5 in which the at least one record of at least one chemical compound includes at least one source document, a location of text associated with the at least one chemical compound, one or more words associated with the at least one chemical compound, and a plurality of surrounding context associated with the at least one chemical compound.

7. The method of claim 1, wherein computing one or more unformulated representations based on the assigned at least one structure representation, further comprises:
   identifying one or more active ingredients associated with the assigned at least one structure representation by separating and comparing a plurality of constituent components associated with the assigned at least one structure representation; and
   neutralizing one or more charges associated with the identified one or more active ingredients.

8. The method of claim 1 in which the single record includes a direct linkage between a plurality of other single records, and a reference to the at least one set of source data.

9. A computer system for identifying and storing at least one representation to at least one chemical compound, comprising:
   one or more hardware processors, one or more computer-readable memories, one or more computer-readable tangible storage medium, and program instructions stored on at least one of the one or more tangible storage medium for execution by at least one of the one or more hardware processors via at least one of the one or more memories, wherein the computer system is capable of performing a method comprising:
   identifying at least one chemical compound associated with at least one set of source data, wherein the source data comprises an unstructured text;
   comparing a plurality of data sources associated with the identified at least one chemical compound;
   converting the at least one set of source data into at least one structure representation based on the compared plurality of data sources and one or more applications of cheminformatics software tools that convert the at least one chemical compound into an identifier chemical formulation or a simplified molecular-input line-entry system string;
   assigning the at least one structure representation to the identified at least one chemical compound associated with the at least one set of source data;
   computing one or more unformulated representations based on the assigned at least one structure representation, by identifying one or more active ingredients and neutralizing one or more charges associated with the one or more active ingredients;
   indexing the computed one or more unformulated representations and the assigned at least one structure representation;
   storing the indexed one or more unformulated representations and the indexed at least one structure representation separately as a single record in a cognitive search and analytics database; and
   in response to a determination that the assigned at least one structure representation includes a plurality of salts, removing the plurality of salts associated with the assigned at least one structure representation.

10. The computer system of claim 9, further comprising:
    receiving a request by a user;
    querying the cognitive search and analytics database based on the received request; and
    in response to retrieving one or more results to the received request from the cognitive search and analytics database, returning the one or more results to the received request to the user.

11. The computer system of claim 10 in which the received request includes at least one of the following:
- at least one chemical compound;
- at least one group of chemical compounds; or
- at least one structure representation associated with a chemical compound or group of chemical compounds.

12. The computer system of claim 9 in which the at least one set of source data further includes one or more sources of secondary internet sources.

13. The computer system of claim 9, wherein identifying at least one chemical compound associated with at least one set of source data, further comprises:
- generating a form of data representation, wherein the generated data representation includes at least one record of at least one chemical compound associated with the at least one set of source data.

14. The computer system of claim 13 in which the at least one record of at least one chemical compound includes at least one source document, a location of text associated with the at least one chemical compound, one or more words associated with the at least one chemical compound, and a plurality of surrounding context associated with the at least one chemical compound.

15. The computer system of claim 9, wherein computing one or more unformulated representations based on the assigned at least one structure representation, further comprises:
- identifying one or more active ingredients associated with the assigned at least one structure representation by separating and comparing a plurality of constituent components associated with the assigned at least one structure representation; and
- neutralizing one or more charges associated with the identified one or more active ingredients.

16. The computer system of claim 9 in which the single record includes a direct linkage between a plurality of other single records, and a reference to the at least one set of source data.

17. A computer program product for identifying and storing at least one representation to at least one chemical compound, comprising:
- one or more computer-readable storage media and program instructions stored on at least one of the one or more tangible storage media, the program instructions executable by a processor to cause the processor to perform a method comprising:
- identifying at least one chemical compound associated with at least one set of source data, wherein the source data comprises an unstructured text;
- comparing a plurality of data sources associated with the identified at least one chemical compound;
- converting the at least one set of source data into at least one structure representation based on the compared plurality of data sources and one or more applications of cheminformatics software tools that convert the at least one chemical compound into an identifier chemical formulation or a simplified molecular-input line-entry system string;
- assigning the at least one structure representation to the identified at least one chemical compound associated with the at least one set of source data;
- computing one or more unformulated representations based on the assigned at least one structure representation, by identifying one or more active ingredients and neutralizing one or more charges associated with the one or more active ingredients;
- indexing the computed one or more unformulated representations and the assigned at least one structure representation;
- storing the indexed one or more unformulated representations and the indexed at least one structure representation separately as a single record in a cognitive search and analytics database; and
- in response to a determination that the assigned at least one structure representation includes a plurality of salts, removing the plurality of salts associated with the assigned at least one structure representation.

18. The computer program product of claim 17, further comprising:
- receiving a request by a user;
- querying the cognitive search and analytics database based on the received request; and
- in response to retrieving one or more results to the received request from the cognitive search and analytics database, returning the one or more results to the received request to the user.

19. The computer program product of claim 17, wherein computing one or more unformulated representations based on the assigned at least one structure representation, further comprises:
- identifying one or more active ingredients associated with the assigned at least one structure representation by separating and comparing a plurality of constituent components associated with the assigned at least one structure representation; and
- neutralizing one or more charges associated with the identified one or more active ingredients.

* * * * *